United States Patent
Waugh et al.

(10) Patent No.: US 8,100,975 B2
(45) Date of Patent: Jan. 24, 2012

(54) INTERVERTEBRAL IMPLANTS WITH ATTACHABLE FLANGES AND METHODS OF USE

(75) Inventors: Lindsey Gardner Waugh, Memphis, TN (US); Jason A Edie, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1566 days.

(21) Appl. No.: 11/463,972

(22) Filed: Aug. 11, 2006

(65) Prior Publication Data

US 2008/0051890 A1    Feb. 28, 2008

(51) Int. Cl.
*A61F 2/44* (2006.01)
(52) U.S. Cl. ............................................. 623/17.16
(58) Field of Classification Search .... 623/17.11–17.16; 24/581.1
See application file for complete search history.

(56) References Cited

U.S. PATENT DOCUMENTS

| | | |
|---|---|---|
| 4,599,086 A | 7/1986 | Doty |
| 4,743,256 A | 5/1988 | Brantigan |
| 4,955,908 A | 9/1990 | Frey et al. |
| 5,236,460 A | 8/1993 | Barber |
| 5,405,391 A | 4/1995 | Hednerson et al. |
| 5,443,515 A | 8/1995 | Cohen et al. |
| 5,458,642 A * | 10/1995 | Beer et al. .................. 623/17.13 |
| 5,702,453 A | 12/1997 | Rabbe et al. |
| 5,888,223 A | 3/1999 | Bray, Jr. |
| 5,916,267 A | 6/1999 | Tienboon |
| 6,044,528 A * | 4/2000 | Schottin .................... 24/265 AL |
| 6,066,175 A | 5/2000 | Henderson et al. |
| 6,235,059 B1 | 5/2001 | Benezech et al. |
| 6,432,106 B1 | 8/2002 | Fraser |
| 6,576,017 B2 | 6/2003 | Foley et al. |
| 6,618,913 B2 * | 9/2003 | Notomi ....................... 24/581.1 |
| 6,682,563 B2 | 1/2004 | Scharf |
| 6,730,127 B2 | 5/2004 | Michelson |
| 2003/0195632 A1* | 10/2003 | Foley et al. ................ 623/17.16 |
| 2004/0193269 A1* | 9/2004 | Fraser et al. ............... 623/17.11 |
| 2005/0075641 A1* | 4/2005 | Singhatat et al. ............... 606/86 |
| 2005/0101960 A1* | 5/2005 | Fiere et al. ...................... 606/72 |

* cited by examiner

*Primary Examiner* — Nicholas Woodall

(57) ABSTRACT

Vertebral implants for spacing apart vertebral members. The implants may include a spacer with a first side and a second side that contact the vertebral members. A sidewall may extend between the first and second sides. Two or more mounts are positioned along the sidewall. A flange may be connected to the spacer at the mounts. The flange extends beyond one or both of the first and second sides to position the spacer relative to the vertebral members. In some embodiments, the spacer further includes one or more insertion features that facilitate insertion of the spacer between the vertebral members.

10 Claims, 8 Drawing Sheets

INTERVERTEBRAL IMPLANTS WITH ATTACHABLE FLANGES AND METHODS OF USE

BACKGROUND

The present invention relates generally to vertebral implants and methods of use, and more particularly to implants and methods that include a flange that may be attached to a periphery of the implant body.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants may further include bone growth material to facilitate fusion of the implant to one or both adjacent vertebral members. The implant should provide for housing the bone growth material, and prevent inadvertent removal of the material from the implant.

SUMMARY

The present application is directed to implants for spacing apart vertebral members. The implants may include a spacer with a first side and a second side that contact the vertebral members. A sidewall may extend between the first and second sides. Two or more mounts are positioned along the sidewall. A flange may be connected to the spacer at the mounts. The flange extends beyond one or both of the first and second sides to position the spacer relative to the vertebral members. In some embodiments, the spacer further includes one or more insertion features that facilitate insertion of the spacer between the vertebral members.

DETAILED DESCRIPTION

Figure 1:
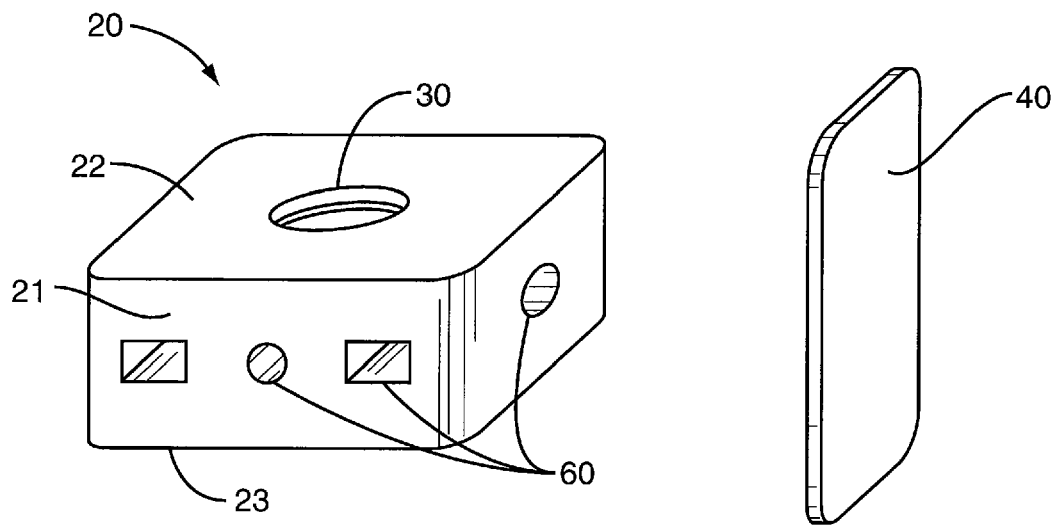
FIG. 1 is an exploded schematic view of a spacer and flange according to one embodiment.
Figure 2:
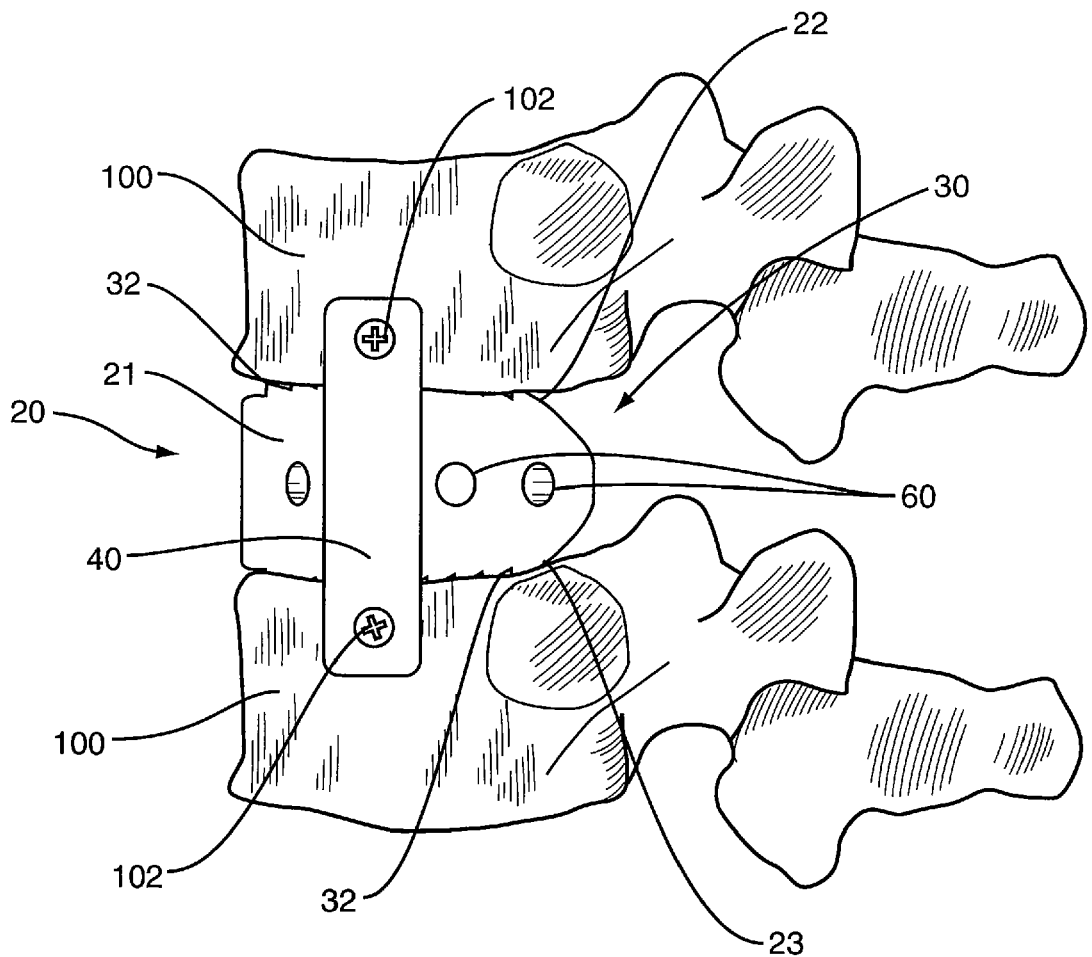
FIG. 2 is a sagittal view of a spacer and flange positioned relative to vertebral members according to one embodiment.

The present application is directed to devices and methods for spacing vertebral members. One context for the devices and methods includes replacement of an intervertebral disc, such as during a discectomy procedure. Another context may include replacement of a vertebral member and intervertebral disc, such as during a corpectomy procedure. FIG. 1 illustrates a schematic representation of a device that includes a spacer 20 with a sidewall that includes one or more mounts 60. The spacer 20 further includes superior and inferior sides 22, 23. The spacer 20 may further include one or more insertion features 30 that facilitate insertion between the vertebral members 100 (FIG. 2). A flange 40 is adapted to selectively attach to a mount 40 to maintain the position of the spacer 20 between the vertebral members 100.

FIG. 2 illustrates a spacer 20 positioned between adjacent vertebral members 100. The superior side 22 contacts the superior vertebral member 100 and the inferior side 23 contacts the inferior vertebral member 100. Insertion features 30 include one or more sections with a reduced height and teeth 32 on the superior and inferior sides 22, 23. Both of these features 30 facilitate an anterior approach into the disc space between the vertebral members 100. A plurality of mounts 60 spaced along the sidewall provide for attachment of the flange 40 at a variety of locations.

Figure 3:
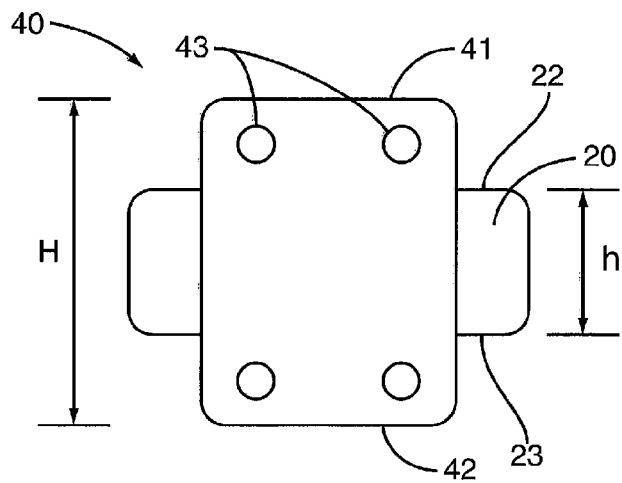
FIG. 3 is a side view of a flange and spacer according to one embodiment.
Figure 5:
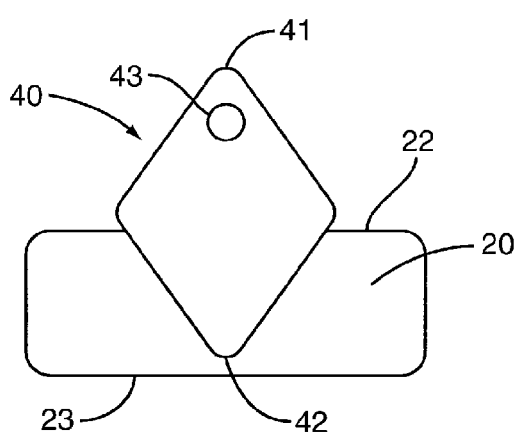
FIG. 5 is a side view of a flange and spacer according to one embodiment.
Figure 6:
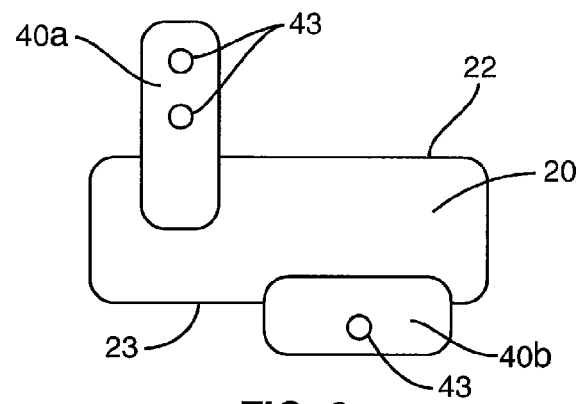
FIG. 6 is a side view of a flange and spacer according to one embodiment.

The flange 40 generally includes a first end 41 and a second end 42 as illustrated in FIG. 3. One or more apertures 43 may extend through the flange 40 to receive fasteners 102 (FIG. 2) to mount the spacer 20 to the vertebral members 100. A height H of the flange 40 is defined between the first and second ends 41, 42. The height H of the flange 40 may be greater than the height h of the spacer 20 to align the apertures 43 at the first and second ends 41, 42 with the vertebral members 100 as illustrated in FIG. 2. FIG. 5 illustrates another embodiment with the second end 42 positioned at the spacer 20 and the first end 41 extending outward from the spacer 20. The first end 41 includes an aperture 43 for connecting with the vertebral member 100. FIG. 6 illustrates another embodiment with the height H of the flange 40 being less than the height h of the spacer 20. The flange 40 is positioned to extend outward from the spacer 20 for connection with the vertebral member 100. In the embodiment of FIG. 6, a first flange 40a extends outward from the superior side 22 and a second flange 40b extends outward from the inferior side 23. In other embodiments (not illustrated), two or more flanges 40 with a height H greater than the spacer height h are mounted to the spacer 20 with each extending outward from the superior and inferior sides 22, 23.

Figure 4:
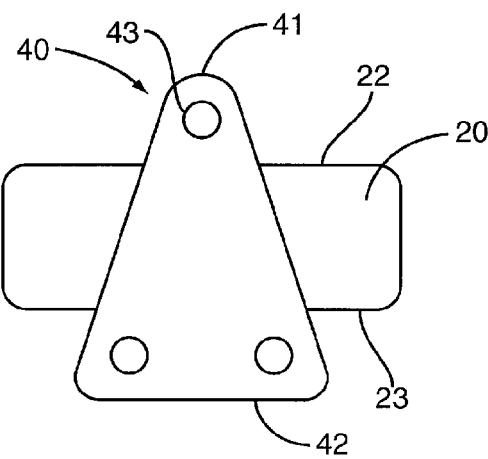
FIG. 4 is a side view of a flange and spacer according to one embodiment.

The shape and size of the flange 40 may vary depending upon the context of use. Examples include but are not limited to a rectangular shape as illustrated in FIGS. 2 and 3, triangular as illustrated in FIG. 4, diamond as illustrated in FIG. 5, and oval of FIG. 6.

Figure 7:
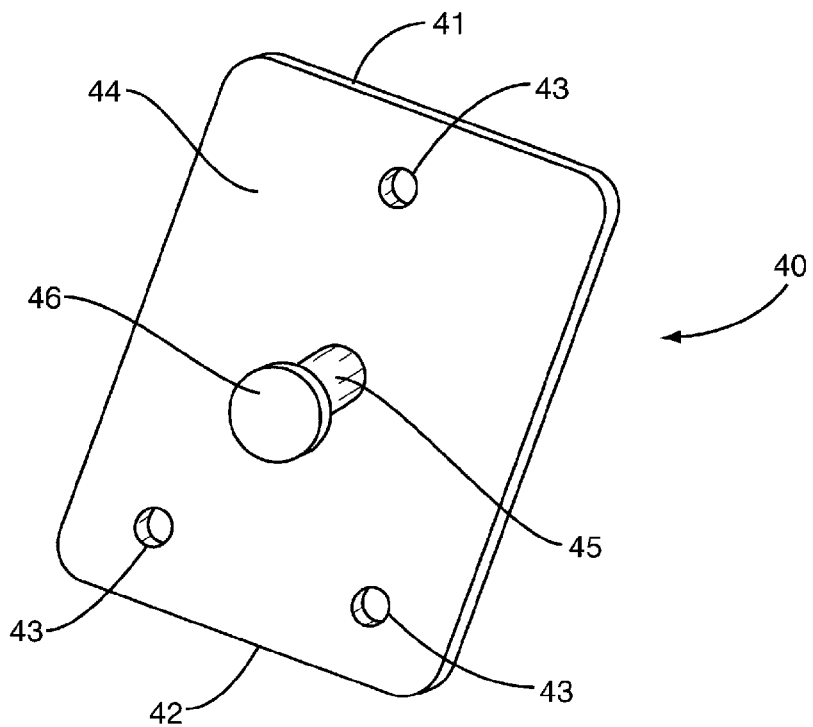
FIG. 7 is a perspective view of an inner side of a flange according to one embodiment.
Figure 8:
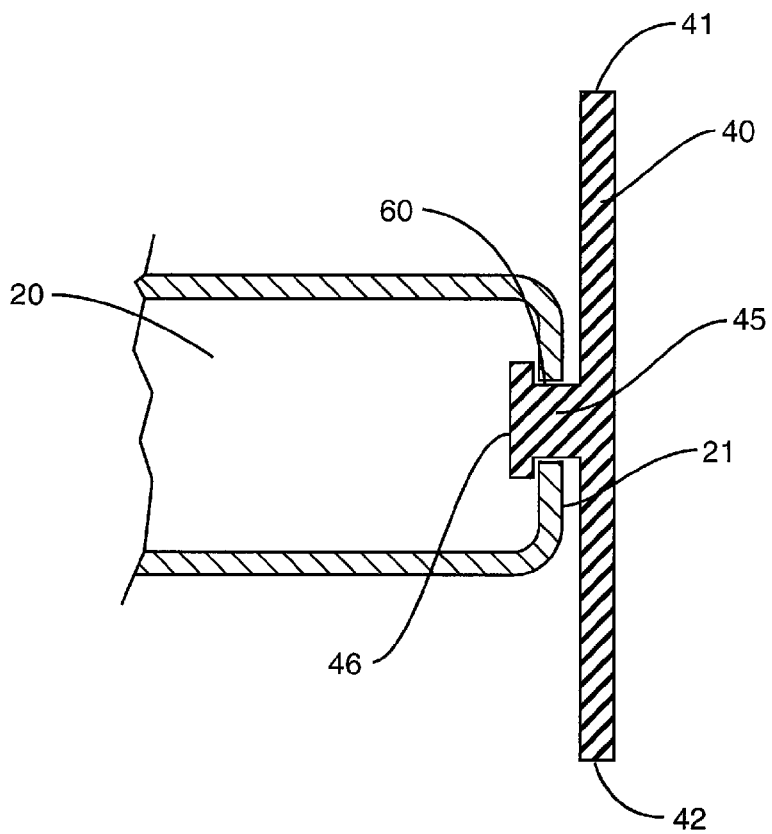
FIG. 8 is a section view of a flange and spacer according to one embodiment.

Flange 40 is constructed to attach to the spacer 20 at one or the mounts 60. FIG. 7 illustrates one embodiment with an extension extending outward from an inner side 44. The extension includes a base 45 and a head 46. Head 46 may be elastic to deform during insertion into the mount 60 and then returns towards the original shape upon insertion through the sidewall 21. FIG. 8 illustrates the flange 40 attached to the spacer 20. The mount 60 includes an aperture sized to receive the extension. The base 45 includes a width that is smaller than or about equal to the aperture with the width of the head 46 being wider than the aperture. During insertion, the flange 40 is moved substantially perpendicular relative to the spacer 20 and the head 46 deforms as it moves through the mount 60. The head 46 than rebounds towards the original size which is larger than the mount 60 thereby maintaining the flange 40 attached to the spacer 20. In one embodiment, the inner side 44 of the flange 40 is in contact with the sidewall 21. In another embodiment, the inner side 44 is spaced away from the sidewall 21 when the flange 40 is mounted.

Figure 9:
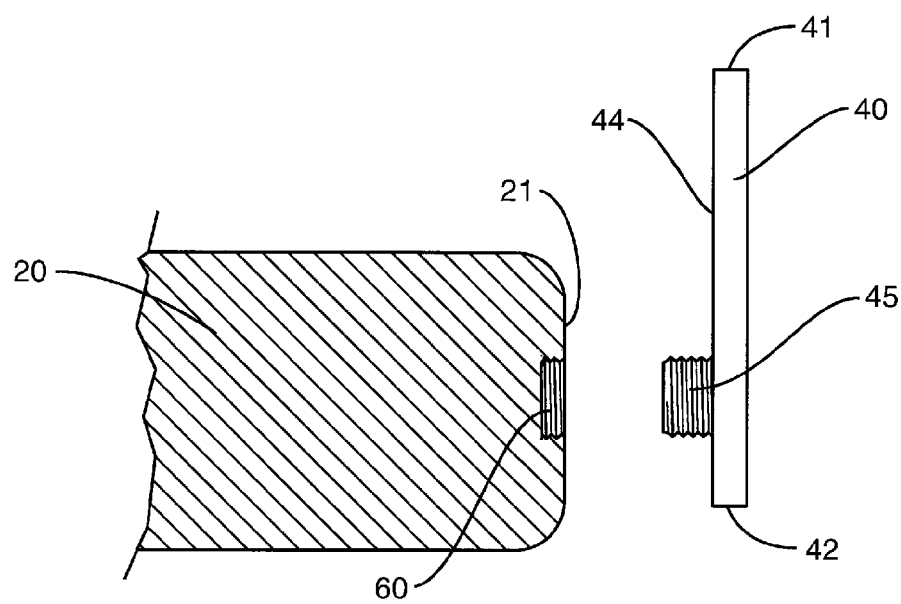
FIG. 9 is an exploded section view of a flange and spacer according to one embodiment.
Figure 10:
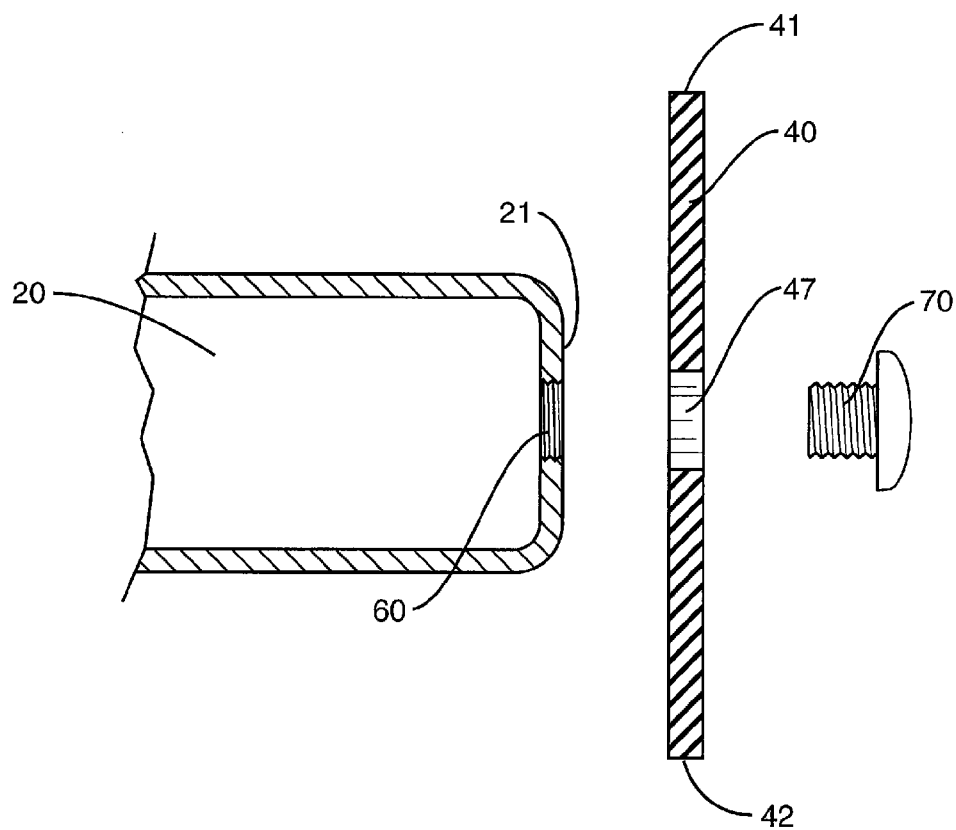
FIG. 10 is an exploded section view of a flange and spacer according to one embodiment.

FIG. 9 illustrates another embodiment with a base 45 that is threaded and extends from inner side 44 of the flange 40. The mount 60 on spacer 20 includes a threaded aperture sized to receive the base 45. In one embodiment, the base 45 is fixed to the flange 40 such that attachment requires rotation of the flange 40. In another embodiment, the base 45 is movably attached to the flange 40 with independent rotation of the base 45 causing attachment (i.e., the flange remains stationary during rotation of the base 45). FIG. 10 illustrates another embodiment with the flange 40 including an aperture 47 that aligns with the mount 60. The aperture 47 may be threaded or unthreaded. A fastener 70 is sized to extend into the aperture 47 and mount 60 to attach the flange 40 to the spacer 20.

Figure 11:
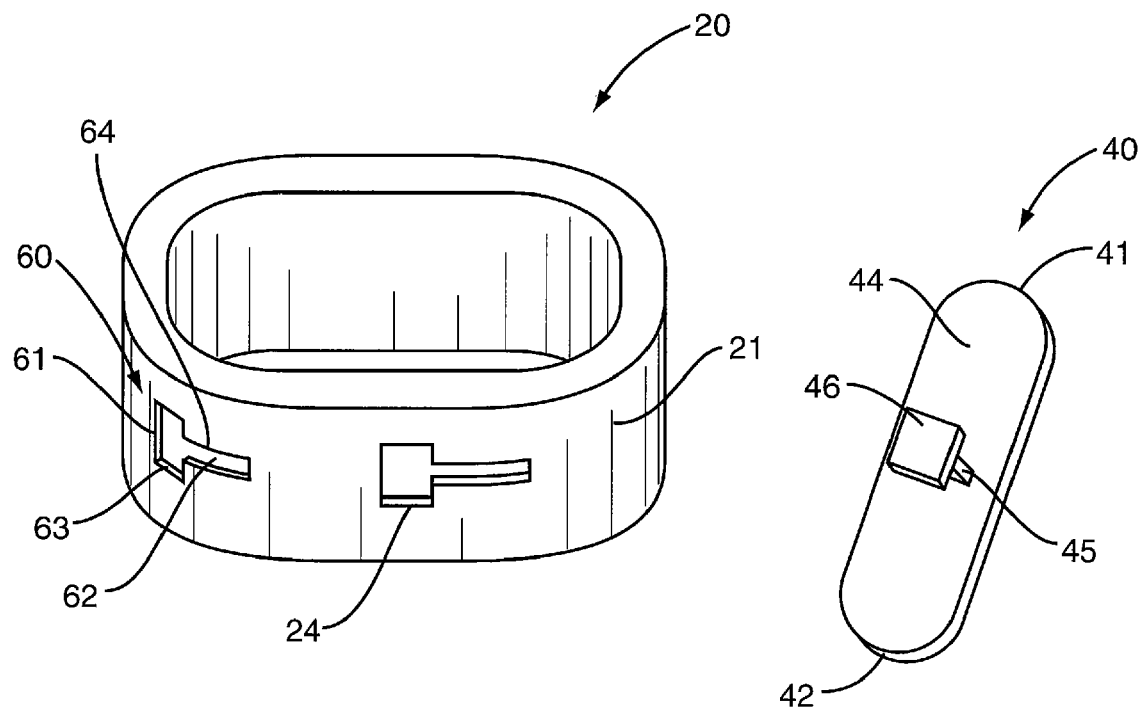
FIG. 11 is a perspective view of a spacer and a flange according to one embodiment.

The flange 40 may further attach to the spacer 20 by sliding. FIG. 11 illustrates an embodiment with the mounts 60 comprising receptacles 61 spaced along the entirety or a limited length of the sidewall 21. The receptacles 61 include a T-shaped slot with a first section 62 sized to receive the base 45 and a second section 63 sized to receive the head 46. During attachment, the head 46 and base 45 are aligned with one of the receptacles 61. The flange 40 is moved laterally thus moving the head 46 into the second section 63 and the base 45 into the first section 62. The first section 62 includes a smaller width than the second section 63 thus preventing the head 46 from being inadvertently removed during motion of the flange 40 relative to the spacer 20. In other embodiments (not illustrated), the receptacle 61 may be aligned in vertical or angled orientations instead of a more horizontal alignment as illustrated in FIG. 11.

The flange 40 may be locked in position by inserting a fastener between the head 46 and the open end of the receptacle 61. In another embodiment, the second section 63 includes a ramped surface 64 that angles away from the open end of the receptacle 61. Moving the flange 40 beyond the ramped surface 64 catches the head 46 within the second section 63 and prevents removal. Examples of flanges that attach with sliding are disclosed in U.S. patent application Ser. No. 11/415,325 filed on May 1, 2006 and entitled "Intervertebral Implants With Covered Inner Chamber and Methods of Use", hereby incorporated by reference.

Two or more mounts 60 may be positioned around the sidewall 21 of the spacer 20. The mounts 60 may be in proximity to one another along a single side of the spacer 20, or may be positioned about the entirety of the sidewall 21. Each of the mounts 60 may be substantially identical to receive the same type of flange 40, or the mounts 60 may be different to receive different types of flanges 40. One or more flanges 40 may be attached to the mounts 60 to position the spacer 20 relative to the vertebral members 100.

The spacer 20 is sized to fit within the intervertebral space between the vertebral members 100. In one embodiment, the spacer 20 replaces an intervertebral disc that has been removed, such as during a discectomy procedure. The spacer 20 includes superior and inferior walls 22, 23 and a sidewall 21. An aperture 26 may extend through a central section of the spacer 20. The spacer 20 may be hollow to contain bone-growth material, or may be substantially solid.

Figure 12:
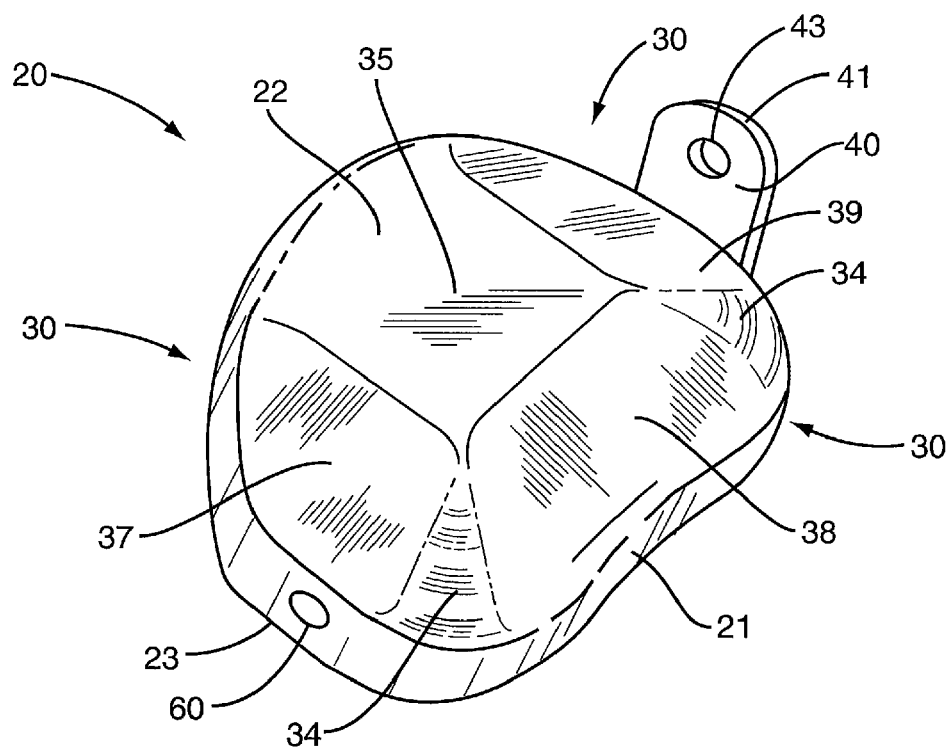
FIG. 12 is a perspective view of a spacer and a flange according to one embodiment.

The spacer 20 may further include one or more insertion features 30 that facilitate insertion into the intervertebral space between the vertebral members 100. One insertion feature 30 includes a tapered section that reduces the height of the spacer 20 as illustrated in FIG. 12. The tapered sections are initially inserted into the vertebral space and act as a wedge to facilitate insertion of the remainder of the spacer 20. Embodiments with multiple tapered sections provide for a single spacer 20 to be used in a variety of different insertion directions into the intervertebral space.

The spacer 20 of FIG. 12 illustrates an embodiment with multiple tapered sections. Sections 37, 38, 39 each taper in a different direction to facilitate insertion of the spacer 20 by three different approaches. Section 37 provides for a first approach direction, section 38 provides a second approach direction, and section 39 a third approach direction. Intermediate sections 34 may be positioned between the sections 37, 38, 39 to prevent abrupt edges that may hamper insertion or potentially cause an injury after insertion into the intervertebral space.

The size, shape, and angle of the tapered sections may vary. Some embodiments include a single tapered surface. Other embodiments feature multiple tapered sections that may include the same or different sizes, shapes, and angles. The tapered sections may extend substantially across the entirety of the superior and/or inferior surfaces 22, 23, or may extend across a limited section. In some embodiments, the tapered surfaces extend up to a substantially flat surface 35.

Figure 13:
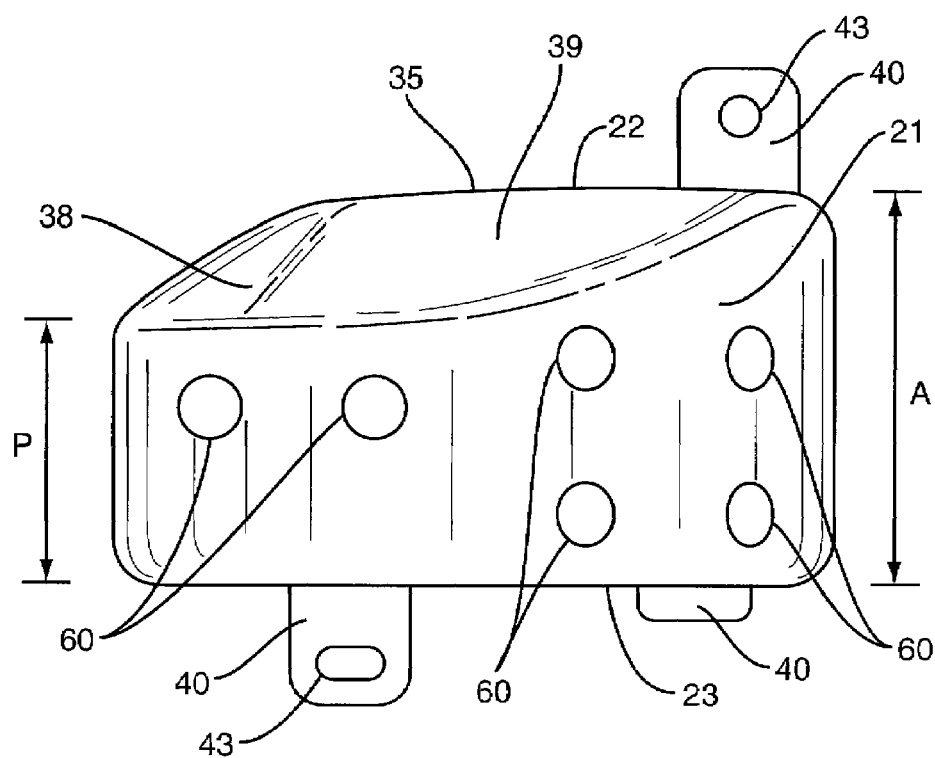
FIG. 13 is a perspective view of a spacer and flanges according to one embodiment.
Figure 14:
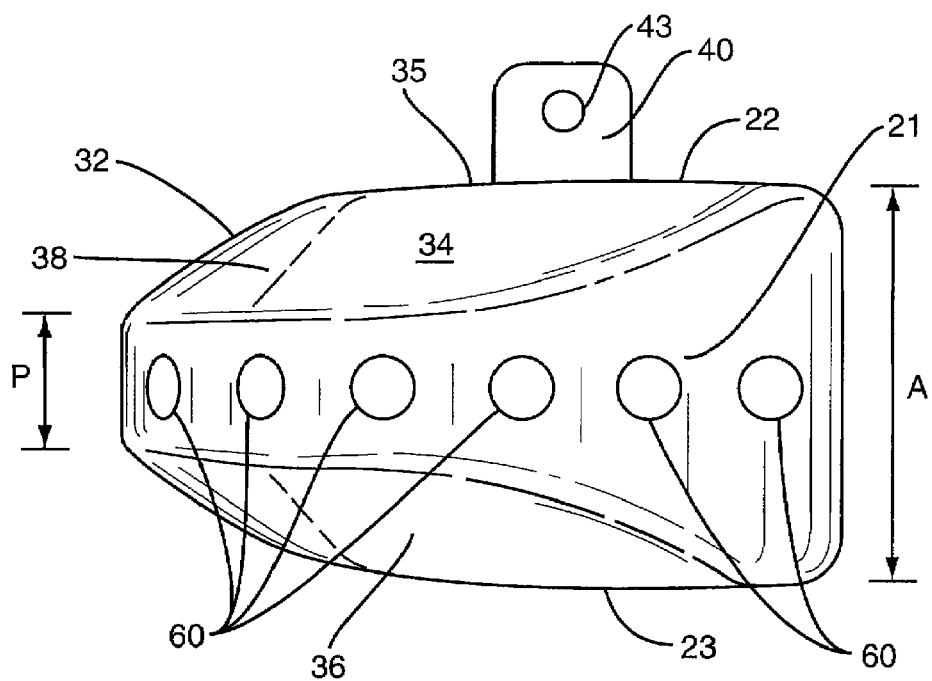
FIG. 14 is a perspective view of a spacer and flange according to one embodiment.

FIG. 13 illustrates an embodiment with tapered sections 38, 39 positioned on the superior side 22. In other embodiments as illustrated in FIG. 14, tapered sections may be arranged on the superior and inferior sides 22, 23. In the embodiments of both FIGS. 13 and 14, the tapered sections 38, 39 cause the posterior height P to be smaller than the anterior height A. This embodiment is intended for insertion with an anterior approach with the reduced height being inserted initially into the intervertebral space. Other embodiments may include the reduced height sections on the anterior side or one or both lateral sides. Embodiments of spacers with tapered sections are disclosed in U.S. patent application Ser. No. 11/412,330 filed on Apr. 27, 2006 and entitled "Intervertebral Implants and Methods of Use" which is herein incorporated by reference.

Spacers 20 with multiple tapered sections allow for insertion from multiple different approaches. Therefore, a single spacer 20 may be used in a variety of different contexts which previously necessitated multiple different spacers. The spacers 20 may further include multiple mounts 60 positioned relative to the tapered sections. Each of the mounts 60 may receive flange 40 at a variety of different positions. By way of example, the spacer 20 may be inserted from a first approach direction with the flange 40 being attached to a first mount 60. The same spacer 20 may also be inserted from a second, different approach direction with the flange 40 attached to a second, different mount 60. Further, multiple flanges 40 may be attached to a single spacer 20.

Figure 15:
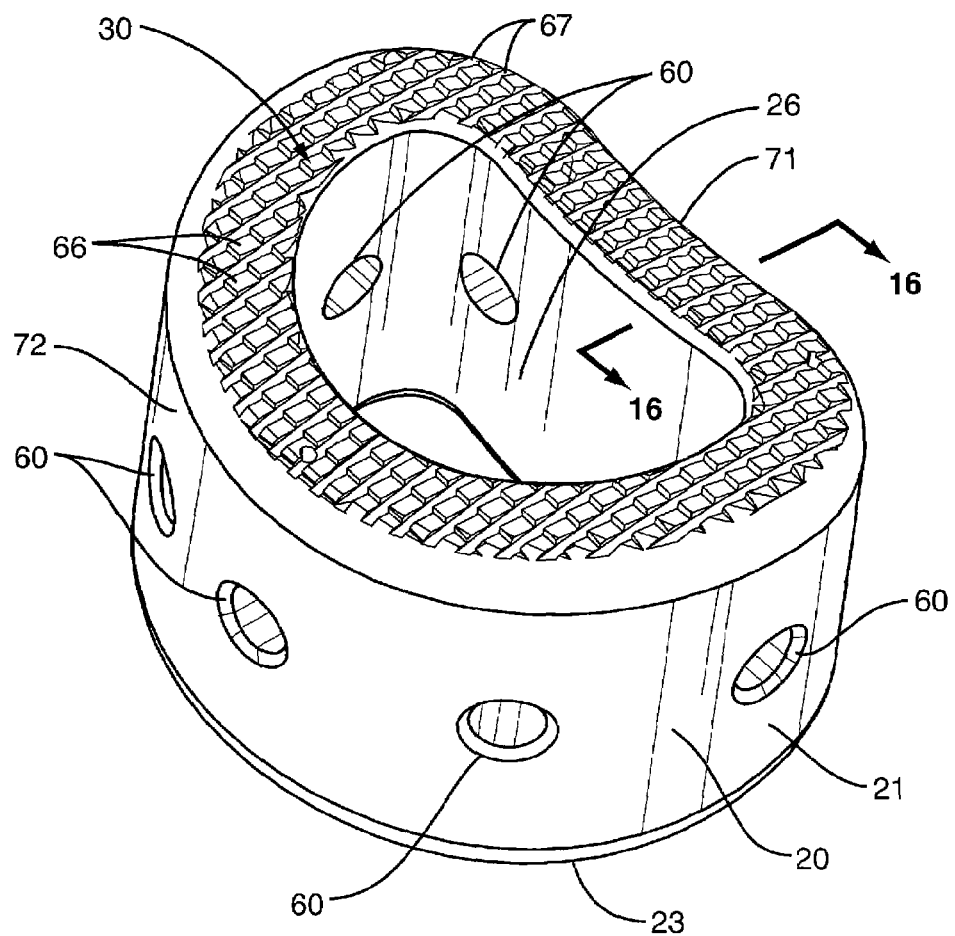
FIG. 15 is a perspective view of a spacer according to one embodiment.
Figure 16:
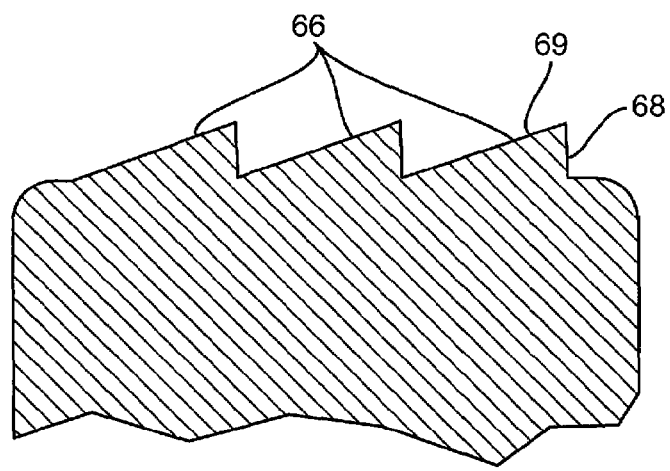
FIG. 16 is a partial section view cut along line 16-16 of FIG. 15 according to one embodiment.

Another insertion feature 30 includes teeth 66 positioned on one or both of the superior and inferior sides 22, 23. Teeth 66 facilitate insertion of the spacer 20 and prevent movement after insertion into the intervertebral space. FIG. 15 illustrates an embodiment with rows of teeth 66 positioned along the superior side 22. The teeth 66 are aligned with gaps 67 positioned between the teeth rows. As illustrated in FIG. 16, each tooth 66 includes a first side 68 and a second angled side 69. The teeth 66 are positioned on the sides 22, 23 to facilitate insertion from a variety of different approaches. In this embodiment, the teeth 66 are angled with facilitate insertion from a lateral approach with a first side 71 being initially inserted into the intervertebral space with the orientation of the first and second sides 68, 69 of each tooth 66 facilitating insertion. An example of teeth 66 are disclosed in U.S. patent application Ser. No. 10/985,237 filed on Nov. 10, 2004 and entitled "Intervertebral Spacer" which is hereby incorporated by reference.

Figure 17:
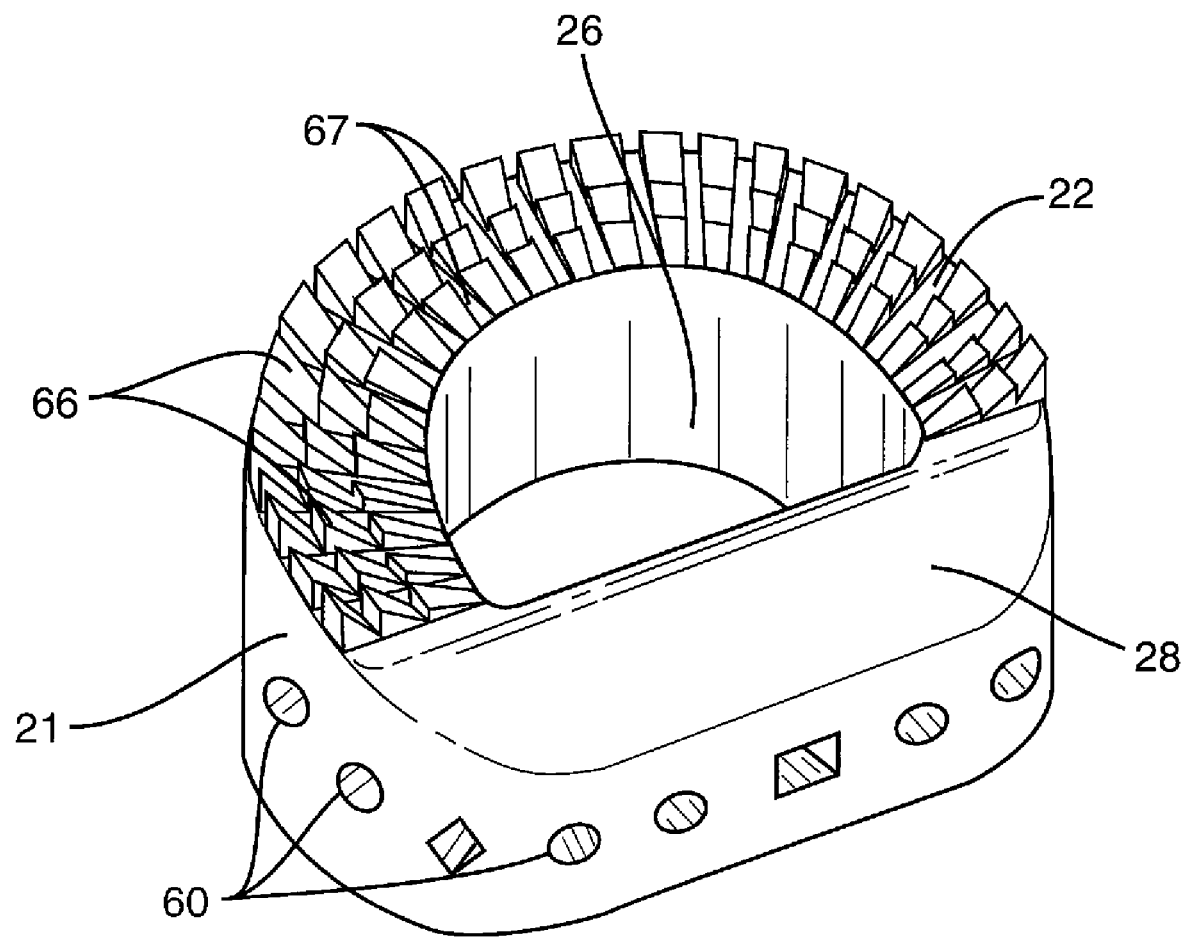
FIG. 17 is a perspective view of a spacer according to one embodiment.

FIG. 17 illustrates another embodiment with teeth 66 aligned in rows that extend outward from a central aperture 26. Teeth 66 are positioned over a section of the superior side 22 with a second section 28 being substantially smooth. The teeth 66 are arranged for inserting the spacer 20 from a variety of different approaches. Mounts 60 positioned along the sidewall 21 provide for attachment positions for one or more flanges 40. The arrangement of the teeth 66 allow for the spacer 20 to be used in a variety of different contexts for insertion with different approaches.

One embodiment of using the spacer 20 comprises determining the desired surgical approach. In some embodiments, the spacer 20 is constructed for insertion with a single approach. In other embodiments, one or more insertion features 30 may allow for multiple surgical approaches. After the spacer 20 is inserted, one or more flanges 40 are attached to the mounts 60. Further, the flanges 40 are attached to one or more of the vertebral members 100 to maintain the position of the spacer 20.

In another embodiment, one or more flanges 40 are attached to the spacer 20 prior to insertion into the intervertebral space. After insertion, the flange 40 is connected to one or more vertebral members 100 to maintain the position of the spacer 20.

Various embodiments include accessing the spine from a variety of different approaches, including posterior, postero-lateral, antero-lateral and lateral approaches. Further, the spacers 20 may be used in various regions of the spine, including the cervical, thoracic, lumbar and/or sacral portions of the spine.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A vertebral implant to space apart vertebral members comprising:
   a spacer including superior and inferior sides configured to contact the vertebral members and a sidewall that extends between the superior and inferior sides;
   a first insertion feature to facilitate insertion of the spacer between the vertebral members in a first direction, the first insertion feature being oriented towards a first section of the sidewall;
   a second insertion feature to facilitate insertion of the spacer between the vertebral members in a second direction, the second insertion feature being oriented towards a second section of the sidewall that is positioned about 90 degrees away from the first section of the sidewall;
   a first mount located on the first section of the sidewall;
   a second mount located on the second section of the sidewall and spaced away from the first mount;
   a flange adapted to attach to the spacer at one of the first mount and the second mount, the flange including an inner side that abuts against at least one of the vertebral members to maintain the position of the spacer relative to the vertebral members;
   wherein the first insertion feature comprises a tapered section that extends from a central area of the spacer to the first section of the sidewall to form a reduced height.

2. The implant of claim 1, wherein the first insertion feature comprises a plurality of teeth that each includes an angled edge that faces towards the first section of the sidewall.

3. The implant of claim 1, wherein the flange includes a greater height than the spacer.

4. The implant of claim 1, wherein the first and second mounts include apertures sized to receive an extension that extends outward from the inner side of the flange.

5. The implant of claim 4, wherein the extension comprises a base and a head, the head including a greater width than the base and the apertures, the head further being deformable to thereby reduce the width during insertion.

6. The implant of claim 1, wherein the flange includes a triangular shape with a first end that extends beyond the superior side and a second end that extends beyond the inferior side when the flange is attached to the spacer.

7. The implant of claim 1, wherein the first mount is different than the second mount.

8. A vertebral implant to space apart vertebral members comprising:
   a spacer including first and second sides configures to contact the vertebral members and a sidewall that extends between the first and second sides;
   a first set of teeth aligned in a first row on the first surface with each of the teeth having a ramped surface that face in a first direction to facilitate insertion of the spacer between the vertebral members;

a second set of teeth aligned in a second row on the first surface with each of the teeth having a ramped surface that face in a second direction to facilitate insertion of the spacer between the vertebral members;

a first mount extending into the sidewall at a first position with a first straight line extending through each of the ramped surfaces of the first set of teeth in the first row also extending through the first mount;

a second mount extending into the sidewall at a second position with a second straight line extending through each of the ramped surfaces of the second set of teeth in the second row also extending through the second mount; and a flange including an extension adapted to connect to either of the first and second mounts with an inner side of the flange contacting against at least one of the vertebral members.

9. The implant of claim 8, wherein the first and second mounts are positioned on opposing sides of the spacer.

10. The implant of claim 8, wherein the spacer further comprises a central aperture that extends through the spacer with the first and second sets of teeth being aligned on opposing sides of the aperture, each of the first and second straight lines extending through the central aperture.

* * * * *